(12) United States Patent
Clark et al.

(10) Patent No.: US 8,226,727 B2
(45) Date of Patent: Jul. 24, 2012

(54) FEMORAL PROSTHESIS

(75) Inventors: Ron Clark, Valparaiso, IN (US); David Blakemore, Warsaw, IN (US); Ross Mack, Valparaiso, IN (US)

(73) Assignee: VOT, LLC, Warsaw, IN (US)

( * ) Notice: Subject to any disclaimer, the term of this patent is extended or adjusted under 35 U.S.C. 154(b) by 182 days.

(21) Appl. No.: 12/393,658

(22) Filed: Feb. 26, 2009

(65) Prior Publication Data
US 2009/0228114 A1     Sep. 10, 2009

Related U.S. Application Data

(60) Provisional application No. 61/067,742, filed on Feb. 29, 2008, provisional application No. 61/067,741, filed on Feb. 29, 2008, provisional application No. 61/067,740, filed on Feb. 29, 2008.

(51) Int. Cl.
*A61F 2/38* (2006.01)

(52) U.S. Cl. .................................................. 623/20.36

(58) Field of Classification Search ............... 623/20.15, 623/20.32, 20.35, 20.29–20.3, 22.46
See application file for complete search history.

(56) References Cited

U.S. PATENT DOCUMENTS

| | | | |
|---|---|---|---|
| 3,852,830 A * | 12/1974 | Marmor ....................... 623/20.3 |
| 4,166,292 A | 9/1979 | Bokros |
| 4,274,163 A * | 6/1981 | Malcom et al. ................. 606/94 |
| 4,711,233 A * | 12/1987 | Brown ............................. 606/81 |
| 4,778,473 A | 10/1988 | Matthews et al. |
| 4,888,024 A * | 12/1989 | Powlan ....................... 623/23.19 |
| 4,892,550 A * | 1/1990 | Huebsch ..................... 623/23.19 |
| 4,963,152 A | 10/1990 | Hofmann et al. |
| 4,969,888 A * | 11/1990 | Scholten et al. ................. 606/94 |
| 5,116,377 A * | 5/1992 | Skripitz et al. ............. 623/23.19 |
| 5,171,276 A * | 12/1992 | Caspari et al. ............. 623/16.11 |
| 5,266,075 A | 11/1993 | Clark et al. |
| 5,314,482 A * | 5/1994 | Goodfellow et al. ....... 623/20.35 |
| 5,336,266 A | 8/1994 | Caspari et al. |
| 5,340,362 A * | 8/1994 | Carbone ..................... 623/23.19 |
| 5,376,123 A * | 12/1994 | Klaue et al. ................. 623/23.19 |
| 5,393,302 A | 2/1995 | Clark et al. |
| 5,405,395 A | 4/1995 | Coates |
| 5,501,687 A * | 3/1996 | Willert et al. .................... 606/94 |
| 5,527,317 A * | 6/1996 | Ashby et al. .................... 606/91 |
| 5,571,204 A * | 11/1996 | Nies ........................... 623/23.19 |
| 5,643,273 A | 7/1997 | Clark |
| 5,693,099 A * | 12/1997 | Harle ......................... 623/23.19 |
| 5,702,446 A * | 12/1997 | Schenck et al. ............ 623/23.55 |

(Continued)

OTHER PUBLICATIONS

International Search Report and Written Opinion dated May 26, 2009 in PCT Application No. PCT/US09/35304.

(Continued)

*Primary Examiner* — Alvin J Stewart
(74) *Attorney, Agent, or Firm* — Heslin Rothenberg Farley & Mesiti P.C.

(57) ABSTRACT

The present invention relates to a femoral prosthesis that includes a cement introduction port which may be used to facilitate delivery or introduction of bone cement into the prosthesis/bone interface after the prosthesis component has been placed on a resurfaced femur bone. The femoral prosthesis may have a keel with undercuts which are configured to assist in controlling the flow of bone cement during implantation and to improve stability of the prosthesis following implantation. The femoral prosthesis is suitable for implantation using arthroscopic, as well as open, surgical procedures. The present prostheses may be used as unicondylar implants in either compartment of the knee or in both compartments of the knee.

20 Claims, 4 Drawing Sheets

U.S. PATENT DOCUMENTS

| | | | |
|---|---|---|---|
| 5,766,256 A | 6/1998 | Oudard et al. | |
| 5,954,747 A | 9/1999 | Clark | |
| 6,017,350 A * | 1/2000 | Long | 606/94 |
| 6,273,891 B1 * | 8/2001 | Masini | 606/91 |
| 6,306,138 B1 | 10/2001 | Clark et al. | |
| 6,306,156 B1 | 10/2001 | Clark | |
| 6,423,096 B1 | 7/2002 | Musset et al. | |
| 6,558,389 B2 | 5/2003 | Clark et al. | |
| 6,723,102 B2 | 4/2004 | Johnson et al. | |
| 6,780,188 B2 | 8/2004 | Clark et al. | |
| 6,821,300 B2 | 11/2004 | Masini | |
| 6,827,739 B2 * | 12/2004 | Griner et al. | 623/16.11 |
| 6,884,246 B1 | 4/2005 | Sonnabend et al. | |
| 6,923,817 B2 | 8/2005 | Carson et al. | |
| 6,966,928 B2 | 11/2005 | Fell et al. | |
| 6,979,336 B2 * | 12/2005 | Durniak | 606/92 |
| 7,083,652 B2 | 8/2006 | McCue et al. | |
| 7,105,027 B2 * | 9/2006 | Lipman et al. | 623/20.29 |
| 7,141,053 B2 * | 11/2006 | Rosa et al. | 606/86 R |
| 7,211,113 B2 * | 5/2007 | Zelener et al. | 623/22.43 |
| 7,258,701 B2 * | 8/2007 | Aram et al. | 623/20.15 |
| 7,297,164 B2 | 11/2007 | Johnson et al. | |
| 7,530,982 B1 * | 5/2009 | Goshert | 606/95 |
| 7,572,293 B2 * | 8/2009 | Rhodes et al. | 623/20.32 |
| 7,862,619 B2 * | 1/2011 | Clark | 623/20.3 |
| 2002/0161448 A1 * | 10/2002 | Hayes et al. | 623/20.32 |
| 2003/0009232 A1 | 1/2003 | Metzger et al. | |
| 2003/0097184 A1 * | 5/2003 | Mitsugi et al. | 623/23.19 |
| 2003/0187513 A1 * | 10/2003 | Durniak | 623/22.12 |
| 2004/0006394 A1 * | 1/2004 | Lipman et al. | 623/20.29 |
| 2004/0039450 A1 * | 2/2004 | Griner et al. | 623/20.31 |
| 2004/0153087 A1 * | 8/2004 | Sanford et al. | 606/88 |
| 2004/0153162 A1 * | 8/2004 | Sanford et al. | 623/20.3 |
| 2004/0167631 A1 | 8/2004 | Luchesi et al. | |
| 2004/0243134 A1 | 12/2004 | Walker et al. | |
| 2005/0137708 A1 * | 6/2005 | Clark | 623/20.15 |
| 2005/0192583 A1 | 9/2005 | Walker et al. | |
| 2005/0192584 A1 | 9/2005 | Walker et al. | |
| 2005/0246027 A1 * | 11/2005 | Metzger et al. | 623/20.15 |
| 2005/0283253 A1 | 12/2005 | Coon et al. | |
| 2006/0052875 A1 | 3/2006 | Bernero et al. | |
| 2006/0235537 A1 | 10/2006 | Kuczynski et al. | |
| 2007/0005142 A1 * | 1/2007 | Rhodes et al. | 623/20.32 |
| 2007/0032876 A1 | 2/2007 | Clark | |
| 2007/0198022 A1 * | 8/2007 | Lang et al. | 606/88 |
| 2007/0213735 A1 | 9/2007 | Saadat et al. | |
| 2007/0288029 A1 * | 12/2007 | Justin et al. | 606/87 |
| 2007/0299532 A1 * | 12/2007 | Rhodes et al. | 623/20.32 |
| 2009/0069899 A1 * | 3/2009 | Klein | 623/22.4 |
| 2009/0198340 A1 * | 8/2009 | Cloutier et al. | 623/20.35 |
| 2009/0204117 A1 * | 8/2009 | Middleton | 606/62 |
| 2009/0228112 A1 * | 9/2009 | Clark et al. | 623/20.32 |
| 2009/0299373 A1 * | 12/2009 | Sisken | 606/92 |
| 2009/0306673 A1 * | 12/2009 | Buma et al. | 606/93 |
| 2010/0211179 A1 * | 8/2010 | Angibaud et al. | 623/20.27 |
| 2010/0217401 A1 * | 8/2010 | de Beaubien | 623/20.34 |

OTHER PUBLICATIONS

International Search Report and Written Opinion dated Jun. 2, 2009 in PCT Application No. PCT/US09/35301.

U.S. Appl. No. 12/393,682, filed Feb. 26, 2009.

* cited by examiner

FEMORAL PROSTHESIS

RELATED APPLICATION

This application claims the benefit of U.S. Provisional Application Ser. No. 61/067,742 filed Feb. 29, 2008; U.S. Provisional Application Ser. No. 61/067,741 filed Feb. 29, 2008; and U.S. Provisional Application Ser. No. 61/067,740 filed Feb. 29, 2008, the entire disclosures of which are incorporated herein by this specific reference.

BACKGROUND OF THE INVENTION

The present invention generally relates to prosthetic implants and, more particularly, to femoral prostheses for knee joints, such as human knee joints.

It has become a common practice to implant medical prostheses to resurfaced articular surfaces of knees, for example, during knee replacement surgery. Many of the prior art prosthetic implants require large incisions to provide adequate access to the joint space to accommodate the implant as well as the surgical tools required during the surgery. In addition, conventional knee replacement procedures often involve resection or removal of substantial amount of bone or cartilage tissue in order to accommodate relatively large prosthetic implant designs typically used today. Such substantial removal of bone can cause increased surgical trauma to a patient and may increase time required for recovery and rehabilitation. In addition, excessive removal of bone tissue may lead to failure of the prosthetic implant due to subsidence thereof into the underlying bone tissue. Unfortunately, this often necessitates additional surgery, for example, revision surgery, in order to replace the failed implant.

Bone cement is typically used to secure implant components to a resurfaced bone. Misalignment of components may occur when too much or too little bone cement is placed on the implant and the implant positioned on the bone surface. If excess bone cement is used, bone cement may escape from between the bone and the edges of the implant requiring additional surgical steps or processes to remove the escaped cement. If the excess or leaked cement is left in the joint space after the surgery, the cement may cause irritation or even injury to the patient, necessitating revision surgery to correct. Alternatively, if too little bone cement is used, the inadequate amounts of bone cement may result in inadequate fixation of the implant to the bone, resulting in the loosening of the implant, necessitating revision surgery to correct.

Caspari et al U.S. Pat. No. 5,336,266 discloses tibial and femoral knee joint prostheses which include open channels through which bone cement can be passed to an inner surface of the implant to at least assist in fixing the implant to the tibia/femur bone. Caspari et al discloses a two piece tibial implant including a polymeric insert fitted into a metal implant body. Caspari et al employs a sharp rim on the implant to form a seal around the cement receiving chamber. In spite of such structure, the Caspari et al devices tend to have problems, for example, with cement leakage, too much or too little cement being injected, and uneven distribution of the cement, which can cause discomfort and/or other harm to the patient and/or revision surgery.

There is still an unmet need for better prosthetic implants, for example, femoral prosthetic implants useful in knee replacement surgery.

SUMMARY OF THE INVENTION

Accordingly, it is an object of the present invention to overcome at least some of the above mentioned disadvantages associated with prior art devices and surgical procedures. The present invention provides new, for example, improved, femoral prosthesis devices for a human knee joint which may be, and are preferably, structured to be implantable by means of arthroscopic surgical techniques as well as conventional, open surgical techniques. The present prosthesis may be used as an unicondylar implant in either compartment of the knee or in both compartments of the knee.

Advantageously, the present devices may be sized and structured to reduce the required size of surgical incisions and/or reduce the amount of bone that must be removed during surgery, when compared to prior art implant devices and surgical procedures.

The devices may be further structured to prohibit or substantially prevent undesirable leakage of bone cement away from the implant, for example, leakage of bone cement into a joint space adjacent the implant. For example, the device may include structure effective to facilitate delivery of bone cement to the appropriate interface region between the implant device and the resurfaced region of the bone.

In addition, the devices of the invention may be structured to reduce occurrence of subsidence of the implant device. For example, the devices may be structured to require or to be used in combination with no more than a minimal, or substantially a minimal, resection of bone such that bone architecture is left substantially intact and better able to adequately support the implants. In one embodiment, the present devices may be used with less resection of bone relative to another implant device, for example, an identical implant device, without one or more of the structural features of the present devices.

Another object of the present invention is to reduce surgical trauma by providing devices, for example, femoral prostheses, that reduce the required size of surgical incisions and/or that reduce the amount of bone that must be removed during implantation when compared to prior art femoral prosthetic devices, for example, which are without one or more structural features of the present devices. Advantageously, the present devices may be surgically implanted into an articular surface of a knee using either conventional open surgical methods or arthroscopic surgical methods. In some preferred embodiments of the invention, the devices comprise femoral prostheses which are structured, for example, sized, shaped or otherwise configured, to be implantable through a single surgical incision, or skin portal, which may be less than about 40 mm, or less than about 30 mm or less than about 25 mm.

Yet another object of the present invention is to provide an implant that, in the event that revision surgery is required, would allow the use of a standard unicompartment replacement knee prosthesis. More specifically, in one aspect of the invention, the implant devices are structured to require a minimal or substantially minimal resection of bone such that the bone architecture is left substantially intact leaving more bone stock, for example, sufficient bone stock, available for use in revision surgery when compared to prior art devices, for example, which are without one or more structural features of the present devices, and prior art surgical procedures.

Accordingly, prosthetic implants, for example, femoral prosthesis devices, are provided. In one useful aspect of the invention, the devices generally comprise a distal region and a proximal region or a proximal fixation region (hereinafter sometimes referred to more simply as "proximal region"), substantially opposing the distal region. The distal region may, and often does, provide a prosthetic articulating surface of a resurfaced bone, for example, femoral bone. The proximal fixation region substantially opposing the distal region is generally structured to interface with, or to face the resurfaced region of the bone, for example, femur bone.

In one aspect of the invention, the device further comprises at least one port positioned to facilitate introduction or injection of bone cement, for example, through the at least one port, to the proximal region. In one embodiment, the at least one port, or each of the ports if more than one port is employed, includes an inlet, an outlet and a closed or substantially closed passageway in the device therebetween, that is between the inlet and the outlet. The proximal region may, and preferably does, include a sidewall, for example, extending proximally from the distal region, and a recessed portion effective for containing bone cement introduced or injected to the proximal region through the at least one port.

More specifically, the device is structured to be effective to facilitate introduction or injection of and containment of bone cement used to facilitate bonding of the device to a resurfaced region of a bone, for example, a femur bone. For example, the at least one port may be positioned proximal or substantially proximal and adjacent to the sidewall and provides structure for receiving and passing bone cement to an appropriate location between the device and the bone, for example, after the device is placed in contact with or on a femur bone. Further, the sidewall and recess or recessed portion provide means for containing the bone cement in the appropriate location and preventing leakage thereof into the joint space. For example, the device may be structured to prevent undesirable extrusion of cement exterior to the device after implantation of the device.

Without wishing to limit the invention to any particular theory of operation, it is believed that the structure and/or location or position of the present at least one port of the present devices is useful in facilitating one or more benefits provided by the present devices, such as providing for enhanced passing of bone cement to an appropriate location between device and bone, enhanced containment of the bone cement, reduced leakage, for example, unwanted leakage, of bone cement around the periphery of the device or implant near the cement port at the bone implant interface, for example, into the joint space and/or reduced extrusion of the bone cement exterior of the device. For example, it is believed that the closed passageway between the inlet and outlet of the present port or ports provides better control of bone cement injection, bone cement containment or positioning between device and bone, bone cement leakage and/or bone cement extrusion outside the device relative to an identical prosthesis device in which the at least one port including a closed passageway is replaced by an open channel. The devices disclosed in Caspari et al U.S. Pat. No. 5,336,266, noted above, employ an open channel for injecting bone cement into the devices.

In a specific embodiment of the invention, the at least one port comprises two ports. Each port may comprise a bore or passageway defined between an inlet and an outlet in communication with the recessed portion. The passageway is defined by a closed bore sidewall. Thus, the passageway is referred to as a closed passageway. The ports, for example, two ports, may be located directly adjacent one another, for example, in a generally side-by-side relationship.

The use of more than one port, for example, two ports, may be advantageous. For example, when a single port is used, the overall diameter of the port is greater for a given area of cement flow relative to using two smaller ports, for example, set side-by-side. Using such a side-by-side dual or two port system, for example, two substantially equally sized ports, allows for less bone resectioning and/or results in less trauma to the patient relative to using a device with a single port to provide the same area for cement flow.

The use of at least dual or two ports may allow the use of a double pronged insertion instrument to hold and/or manipulate the device or implant during surgery. A dual pronged instrument may provide a better grip and/or allow for finer control of the device or implant during surgery. Dual or two closed ports may allow irrigation and/or suction of the implant bone interface. Pulse lavage may be used effectively.

When the device is implanted into the femur bone, the at least one port may be, and often is, located at an anterior region of the joint, for example, the knee joint.

In another especially advantageous aspect of the invention, the sidewall of the proximal region substantially circumscribes or substantially entirely circumscribes the recessed portion. Thus, in one embodiment, the proximal region may be considered to have a peripheral sidewall. Furthermore, the recessed portion may be defined by a generally concave surface surrounded by the sidewall. In some embodiments, the sidewall comprises a lateral portion, a medial portion, an anterior portion and a posterior portion. In one embodiment, the at least one port may extend through the sidewall, preferably through the anterior portion of the sidewall.

Further, the proximal region may further include at least one of a post, keel, or other structure effective to enhance fixation of the device to the resurfaced region of the bone.

For example, in some embodiments, the proximal region further includes a post connected to and extending away from, for example, proximally away from, the recessed portion. The post may have a substantially cruciate cross-section for enhancing fixation of the device to a resurfaced region of a bone and/or for providing structure for facilitating containment of bone cement at the bone/implant interface. In other embodiments, the post may have a circular cross-section, or other suitably shaped cross-section, for example, to allow the post to function as described herein.

In addition, in some embodiments, the proximal region may further include a keel which is connected to and extends away from the recessed portion. The keel may be, and often is, structured to enhance anchoring of the device to the resurfaced region of a bone. The keel may be further structured to be effective in controlling flow of bone cement during the introduction of the bone cement through the port or ports. For example, the keel may include at least one opening or undercut portion through which bone cement may pass. The at least one opening may be bounded in part by the recessed portion. The opening or openings or undercut or undercuts in the keel may be effective to promote substantially uniform distribution of bone cement in the recessed region. For example, the openings or undercuts permit bone cement to penetrate under or through the keel, thereby providing additional fixation and stability during and/or following implantation of the device.

Various embodiments of the present invention are described in detail in the detailed description and additional disclosure below. Any feature or combination of features described herein are included within the scope of the present invention provided that the features included in any such combination are not mutually inconsistent as will be apparent from the context of this specification, and the knowledge of one of ordinary skill in the art. In addition, any feature or combination of features may be specifically excluded from any embodiment of the present invention. Additional advantages and aspects of the present invention are apparent in the following detailed description, drawings and examples.

Many of the aspects and advantages of the present invention may be more clearly understood and appreciated with reference to the following Detailed Description and accompanying drawings.

DETAILED DESCRIPTION

Turning now to the drawings, an embodiment of a femoral prosthesis device in accordance with the invention, for surgical introduction to a resurfaced articular surface of a femur bone, is generally shown at 10.

Resurfacing of the femur bone in preparation for implantation of femoral prosthesis device 10 may be performed using conventional techniques, for example, conventional, open surgical techniques. In one embodiment, such preparation may be performed using the arthroscopic surgical devices and methods described in co-pending U.S. provisional patent application Ser. No. 61/067,741, filed Feb. 29, 2008, entitled INSTRUMENTS AND METHOD FOR ARTHROSCOPY OF THE KNEE and commonly owned herewith, the entire disclosure of said application being incorporated herein in its entirety by this specific reference.

The prosthesis device 10 generally comprises a distal region 12 having a generally convex surface approximating a curvature of a femoral condyle and disposed for articulating with a tibial prosthesis (not shown). The device 10 further comprises a proximal region 14 which substantially opposes the distal region 12 and is structured to interface with a resurfaced region of a femur bone. The proximal region 14 includes a generally concave recessed portion 18. The proximal region 14 is structured to receive and contain bone cement during attachment of the device 10 to a femur bone.

In one especially advantageous aspect of the present invention, the device 10 is structured to be effective to facilitate introduction or injection and containment of bone cement during the surgical implantation procedure. Bone cement useful with the present invention may be any suitable bone cement known to those of skill in the art. For example, the bone cement may be a grout-like material, such as polymethyl methacrylate material and/or other suitable biocompatible material known to those of skill in the art which is effective to provide long term, for example, permanent or substantially permanent, fixation of a prosthesis to a surface of a bone.

Figure 1:
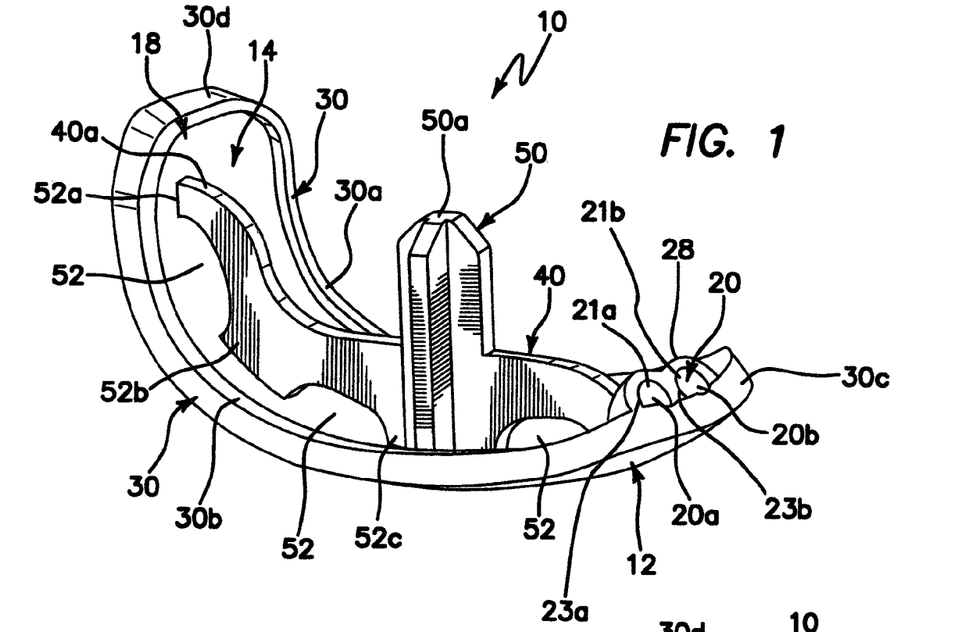
FIGS. 1 and 2 are perspective views of a femoral prosthesis device in accordance with the invention, the device including a generally convex distal region and a proximal region structured to interface with a resurfaced region of a femur bone.
Figure 1A:
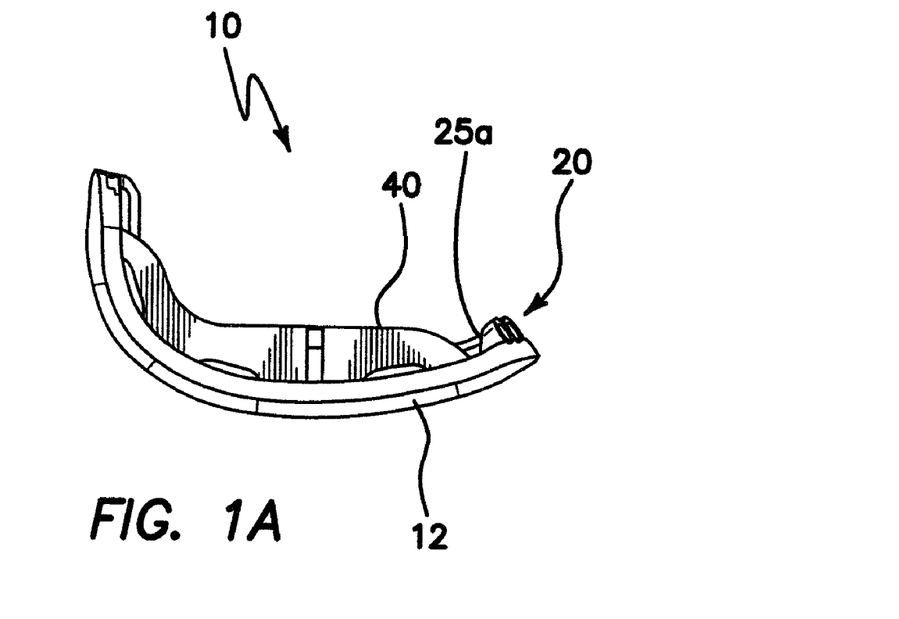
FIGS. 1A and 1B are a side view and a front view, respectively, of the device shown in FIGS. 1 and 2.
Figure 1B:
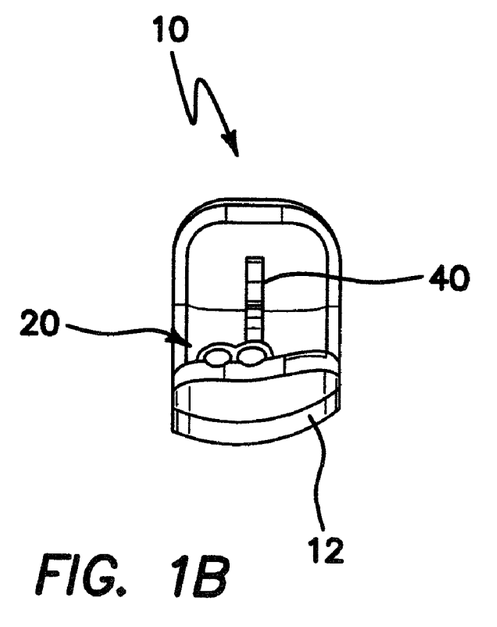
Figure 2:
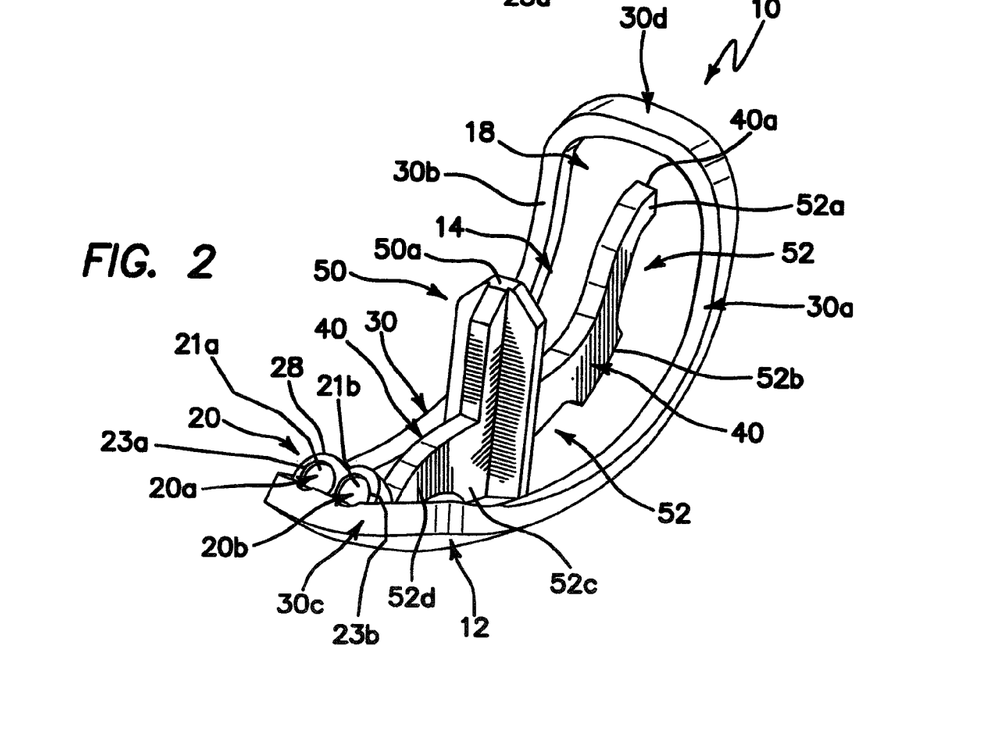
Figure 3:
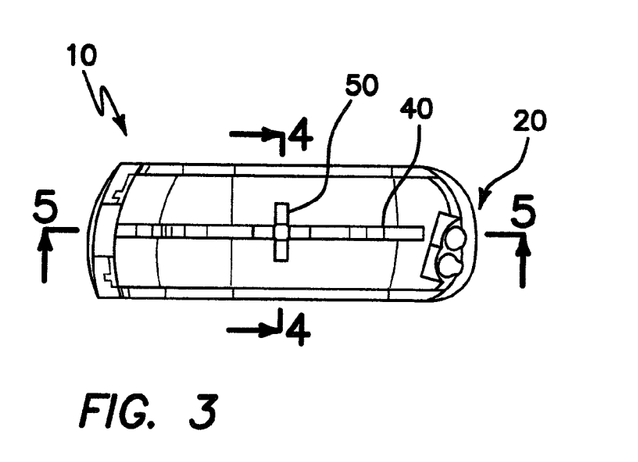
FIG. 3 is a top view of the device shown in FIGS. 1 and 2.
Figure 4:
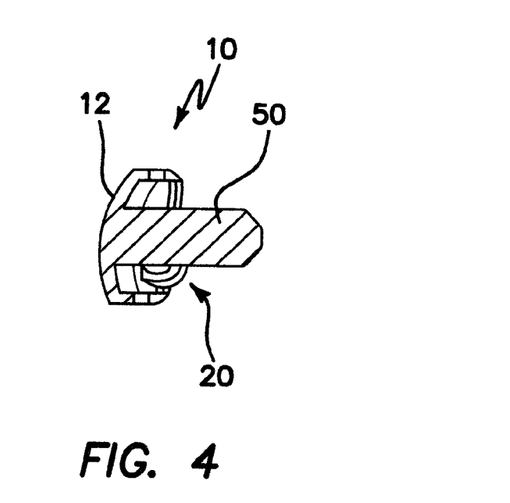
FIG. 4 is a cross-sectional view of the device shown in FIGS. 1 and 2 taken along line 4-4 of FIG. 3.
Figure 5:
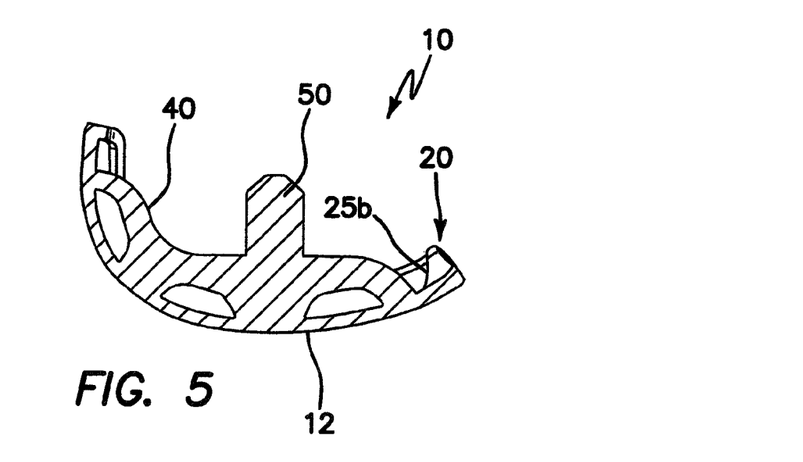
FIG. 5 is a cross-sectional view of the device shown in FIGS. 1 and 2 taken alone line 5-5 of FIG. 3.

For example, in the shown embodiment, the proximal region 14 further comprises structure for facilitating introduction of bone cement to the proximal region 14. More specifically, the device 10 may comprise a port structure, shown generally at 20, including at least one port, for example, two ports 20a and 20b, for facilitating introduction or injection of bone cement to the proximal region 14. The ports 20a and 20b are defined by bores extending through a surface region, for example, a raised surface region 28, of the device 10. The ports 20a and 20b include passageways defined by closed bore sidewalls 21a and 21b, respectively, between inlets 23a and 23b, respectively and outlets 25a (FIG. 1A) and 25b (FIG. 5), respectively. In this embodiment, the ports 20a and 20b are disposed substantially directly adjacent one another, for example, in a generally side-by-side relationship. The ports 20a and 20b are appropriately sized and positioned to facilitate introduction or injection of a suitable bone cement to the bone/implant interface during surgical implantation of the device 10 to the resurfaced region of a femur bone. Each of the ports 20a and 20b has an inlet 23a, 23b away from or outside of the recessed portion 18, and an outlet 25a, 25b through which bone cement passes to be placed in the recessed portion 18. Each of the ports 20a and 20b is oriented so that the passageway slants or slopes distally from the outlet to the inlet. This orientation may facilitate injection of the bone cement and/or containment of the bone cement in the desired location.

More specifically, the ports 20a and 20b may be positioned generally outside of the patella-femoral articulation region of the knee joint when the device 10 is implanted or affixed to the resurfaced region of a femur bone. The ports 20a and 20b may be somewhat offset from a center of the prosthesis device 10. For example, the ports 20a and 20b are positioned in a joint lateral configuration, or away from the joint middle or center, of the device 10. Although two ports 20a and 20b are shown in the drawings, in other embodiments of the invention not shown, the device 10 may comprise only one port or, alternatively, three or more ports. All such embodiments are included within the scope of the present invention.

The introduction or injection of the bone cement or bone cement material may be achieved through a pressurizing syringe or similar fluid mover. The bone cement injected may be a highly viscous material or a less viscous or a more fluid material, for example, relative to the highly viscous bone cement material conventionally introduced to bond an implant to bone. Injecting a more fluid material, such as a material which is flowable or readily flowable at normal or atmospheric pressure under the influence of gravity, is different from injecting highly viscous material, which is not readily flowable at such conditions. In one embodiment, the fluid or more fluid bone cement material has a viscosity (at room temperatures) in a range of about 5,000 centipoise or less to about 50,000 centipoise or about 100,000 centipoise. The injected fluid bone cement material has increased effectiveness, for example, relative to highly viscous bone cement material, for example, injected highly viscous bone cement material, in filling interstitials or small regions between the prosthesis device and the bone, and/or in bonding with mating surfaces.

In the past, a surgeon often had to wait a period of time for the bone cement to set-up or harden sufficiently to allow the surgeon to handle the cement effectively. Such "set up" bone cement, once applied, tends to have or has reduced bonding ability.

The present invention allows the surgeon to take advantage of bone cement in a more fluid state. Such more fluid bone cement material, for example, more fluid bone cement material injected through one or more ports including closed passageways in the present prosthesis device, allows the pores in the bone to be filled with bonding material, as well as providing more adhesive properties to the implant itself. A marked or substantial increase in cement bond strength relative to conventional thumb packing techniques with "set up" bone cement have been shown when more fluid bone cement material is injected, for example, using the prosthesis devices of the present invention.

The proximal region 14 of the device 10 further comprises a sidewall 30, which may include a lateral portion 30*a*, a medial portion 30*b*, an anterior portion 30*c*, and a posterior portion 30*d*. The sidewall may substantially entirely circumscribe the recessed portion 18. The sidewall 30 may be structured to function, at least in part, to facilitate containment of bone cement at the bone/implant interface. In the shown embodiment, the raised surface region 28 and ports 20*a* and 20*b* are located proximal to the sidewall 30, more specifically, proximal and adjacent to the anterior portion 30*c* of the sidewall 30.

Preferably, the sidewall 30 forms a proximally extending structure which substantially or entirely circumscribes the recessed portion 18, and, thus, can be considered a peripheral sidewall. The sidewall 30 is preferably structured to be effective to substantially contain flowable cement or bone cement introduced through the introduction ports 20*a* and 20*b*, or at least facilitate containment of such cement and prevent undesirable extrusion thereof exterior to the prosthesis device 10 for example, outside of the recessed portion 18, after implantation of the device 10. Although in the shown embodiment, the sidewall 30 substantially entirely circumscribes the recessed portion 18, in other embodiments not shown, the sidewall 30 may be discontinuous, for example, may include breaks or disruptions therein, or may extend along only one or more separate portions of the device 10. All such embodiments are included within the scope of the present invention.

An arthroscope may be utilized to visualize cement or bone cement extrusion. Any excess cement may be removed prior to curing thereof, for example, less than about 10 minutes after introduction of the cement.

The device 10 further comprises a keel 40 and a post 50 connected to and extending away proximally from the recessed portion 18.

The keel 40 may be structured to enhance stability of the device 10 with respect to the bone, and/or enhance anchoring of the device 10 to the bone.

In an especially advantageous aspect of the invention, the keel 40 is structured to control flow, or at least assist in controlling flow, of bone cement. For example, the keel 40 may include at least one opening 52 through which bone cement may pass or flow. For example, in the shown embodiment, the keel 40 is connected to the recessed portion 18 at four spaced apart locations 52*a*, 52*b*, 52*c* and 52*d*, which define openings 52 therebetween. The keel 40 may be structured to enhance substantially uniform distribution of the bone cement at the bone/implant interface. For example, the openings 52 permit fluid bone cement to penetrate under or through the keel 40, thereby providing additional fixation and stability during and/or following implantation of the device 10.

In some embodiments, the openings 52 vary in number, size and/or shape to optimize flow and/or uniform distribution of bone cement. In some embodiments, the openings or undercuts are optimized to permit bone cement to be "thumb packed" or manually pressed through the keel 40 to assure good surface coverage by the cement, to remove voids and to provide that the cement is effectively bonded to the device.

The keel may have a shape and/or structure effective to mechanically anchor the bone cement. For example, the keel may include a T-shaped cross section positioned so that the transverse portion or widest portion of the T-shaped cross section of the keel is located proximally, that is at or near a proximal end of the keel, i.e., the end of the keel extending proximally from the recessed portion of the proximal region, and prevents movement up and out of the bone cement bed when the device is implanted.

Figure 6:
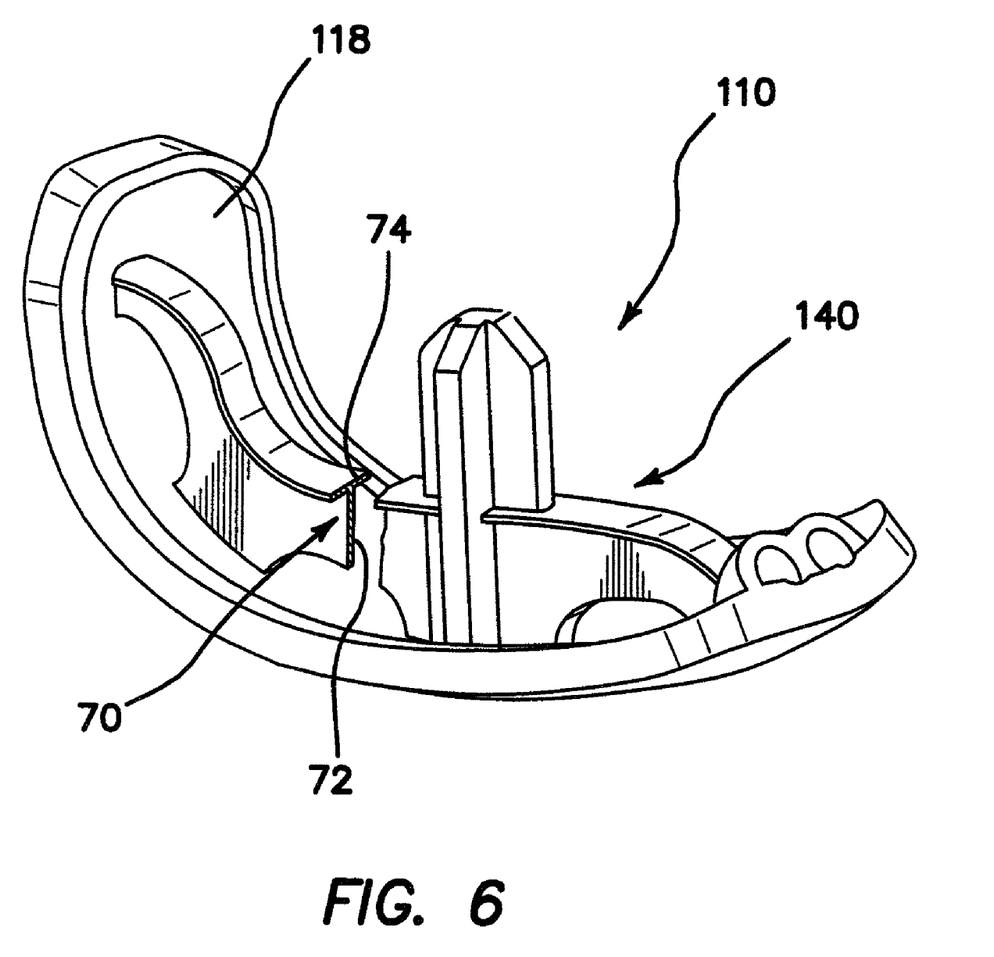
FIG. 6 is a perspective view, partly in cross-section, of an alternate femoral prosthesis device in accordance with the invention.

FIG. 6 shows an alternate femoral prosthesis device 110 in accordance with the present invention which includes an example of a keel having a T-shaped cross-section. Elements in the alternate femoral prosthesis device 110 which correspond to elements in the femoral device 10 are indicated by the same reference numeral increased by 100. Except as set forth herein, alternate femoral prosthesis device 110 is structured and functions similarly to femoral prosthesis device 10.

The primary, and even substantially the sole, difference between alternate femoral prosthesis device 110 and device 10 is the shape of the cross-section of keel 140. Specifically, keel 140 has a substantially T-shaped cross-section, shown as 70, extending proximally from recessed portion 118. The cross-section 70 of keel 140 includes a generally straight or vertical portion 72, and a transverse portion 74, which is wider (in a side to side direction as shown in FIG. 6) than the straight portion 72, and is often the widest portion of the T-shaped cross-section 70.

The T-shaped cross-section 70 of keel 140 is effective in mechanically anchoring the bone cement, for example, in preventing movement of the device 110 up and out of the bone cement bed when the device 110 is implanted.

Advantageously, the configuration and dimensions of the openings 52 may vary to enhance, or even optimize, the flow and/or distribution of bone cement. For example, openings 52 may vary in size, geometric shapes and/or dimensions to effectively allow bone cement to flow throughout the proximal portion or region 14 of the implant or device 10.

In the shown embodiment, the post 50 extends proximately or proximally of the keel 40. The proximal-most surface 50*a* of the post 50 may be substantially flush or at substantially the same height with a proximal-most surface 40*a* of the keel 40 with the post oriented vertically. The post 50 has a cruciate (cross-shaped) cross-section, although it is to be appreciated that the post may have a cross-section of a different geometric shape. The post 50 is preferably structured and positioned to enhance anchoring of the device 10 while maintaining a low profile configuration thereto. In other embodiments of the invention not shown, the post 50 may have a circular cross-section, or other suitably shaped cross-sectional shape. All such embodiments are included within the scope of the present invention.

As shown in the drawings, the device 10 is a single unitary structure and has no moving parts. The device 10 is made of a durable, biocompatible material. Examples of suitable materials include, without limitation, Co—Cr alloy cast conforming to ASTM F75 Specification. In an exemplary embodiment of the present device, the device 10 is available in three sizes, for example, a length, at its widest portion, of about 45 mm, about 50 mm, and about 54 mm, and having either a full or partial post, with a partial post being a post extending level with a proximal most surface of the keel, as discussed elsewhere herein.

Reference to the following U.S. Patents and Published Patent Applications may provide additional disclosure which may be helpful in understanding one or more aspects of the present invention, each of said patents and publications being incorporated herein in its entirety by this specific reference: Bokros, U.S. Pat. No. 4,166,292; Matthews et al., U.S. Pat. No. 4,778,473; Hofmann et al., U.S. Pat. No. 4,963,152; Caspari et al., U.S. Pat. No. 5,171,276; Clark et al., U.S. Pat. No. 5,266,075; Clark et al., U.S. Pat. No. 5,393,302; Coates, U.S. Pat. No. 5,405,395; Clark, U.S. Pat. No. 5,643,273; Oudard et al., U.S. Pat. No. 5,766,256; Clark, U.S. Pat. No.

5,954,747; Clark et al., U.S. Pat. No. 6,306,138; Clark, U.S. Pat. No. 6,306,156; Musset et al., U.S. Pat. No. 6,423,096; Clark et al., U.S. Pat. No. 6,558,389; Johnson et al., U.S. Pat. No. 6,723,102; Clark et al., U.S. Pat. No. 6,780,188; Masini, U.S. Pat. No. 6,821,300; Sonnabend et al., U.S. Pat. No. 6,884,246; Carson et al., U.S. Pat. No. 6,923,817; Fell et al., U.S. Pat. No. 6,966,928; McCue et al., U.S. Pat. No. 7,083,652; Lipman et al., U.S. Pat. No. 7,105,027; Rosa et al., U.S. Pat. No. 7,141,053; Johnson et al., U.S. Pat. No. 7,297,164; Hayes, JR, et al., U.S. Publication No. 2002/0161448; Metzger et al., U.S. Publication No. 2003/0009232; Walker et al., U.S. Publication No. 2004/0243134; Walker et al., 2005/0192583; Walker et al., U.S. Publication No. 2005/0192584; Bernero et al., U.S. Publication No. 2006/0052875; Saadat et al., U.S. Publication No. 2007/0213735; Justin et al., U.S. Publication No. 2007/0288029.

While this invention has been described with respect to various specific examples and embodiments, it is to be understood that the invention is not limited thereto and that it can be variously practiced.

What is claimed is:

1. An implant device, comprising:
    a distal region comprising an articulating surface;
    a proximal region connected to the distal region by a sidewall, the proximal region substantially opposing the distal region and comprising a cement contacting surface, the sidewall extending from the proximal region and forming a continuous boundary surrounding the cement contacting surface;
    at least one port comprising an inlet, an outlet and a closed passageway extending from the inlet to the outlet, the at least one port located substantially at the proximal region and disposed on an anterior aspect of the implant device and at least partially proximal to an anterior portion of the sidewall for the introduction of flowable bone cement to the cement contacting surface; and
    a keel connected to the cement contacting surface, the keel extending from a posterior portion to an anterior portion of the cement contacting surface along a midline of the device and extending away from the cement contacting surface.

2. The device of claim 1 wherein the proximal region further includes a post connected to and extending away from the cement contacting surface.

3. The device of claim 2 wherein the post has a substantially cruciate cross-section.

4. The device of claim 2 wherein the post is integrally formed with the keel.

5. The device of claim 1 further comprising at least one opening formed at least in part in the keel.

6. The device of claim 5 wherein the at least one opening is formed between the keel and the cement contacting surface.

7. The device of claim 1 wherein the keel has a T-shaped cross-section with a transverse portion positioned so that the transverse portion is located at or near a proximal end of the keel to create a uniform mantle of cement.

8. The device of claim 1 wherein the at least one port comprises two ports.

9. The device of claim 1 wherein the at least one port extends through the sidewall.

10. The device of claim 1 wherein the at least one port comprises two ports located substantially proximal to the sidewall.

11. The device of claim 1 wherein the at least one port comprises two ports positioned in a substantially side-by-side relationship.

12. The device of claim 1 wherein the proximal region generally conforms to a resurfaced region of a femur bone.

13. The device of claim 12 which is sized and adapted so as, together with a tibial implant device, to provide a partial knee replacement.

14. The device of claim 1 which is a single unitary structure.

15. A femoral implant device, comprising:
    a distal region comprising a curved articulating surface
    a proximal region connected to the distal region by a sidewall, the proximal region substantially opposing the distal region and comprising a cement contacting surface, the sidewall extending away from the proximal region and forming a continuous boundary surrounding the cement contacting surface;
    at least one port comprising an inlet, an outlet and a closed passageway extending from the inlet to the outlet, the at least one port located substantially at the proximal region and disposed on an anterior aspect of the implant device and at least partially proximal to an anterior portion of the sidewall for the introduction of flowable bone cement to the cement contacting surface; and
    a keel connected to the cement contacting surface, the keel extending from a posterior aspect to an anterior aspect of the cement contacting surface along a midline of the device and extending away from the cement contacting surface.

16. The device of claim 15 wherein the proximal region further includes a post connected to and extending proximally away from the cement contacting surface.

17. The device of claim 16 wherein the post is integrally formed with the keel.

18. The device of claim 15 comprising two side-by-side ports disposed on the anterior aspect of the device and proximal to the sidewall.

19. The device of claim 15 which is sized and adapted so as, together with a tibial implant device, to provide a partial knee replacement.

20. The device of claim 15 which is a single unitary structure.

* * * * *